United States Patent
Brannan

(10) Patent No.: US 9,814,525 B2
(45) Date of Patent: Nov. 14, 2017

(54) SYSTEM AND METHOD FOR ABLATION PROCEDURE MONITORING USING ELECTRODES

(71) Applicant: COVIDIEN LP, Mansfield, MA (US)

(72) Inventor: Joseph D. Brannan, Erie, CO (US)

(73) Assignee: COVIDIEN LP, Mansfield, MA (US)

( * ) Notice: Subject to any disclaimer, the term of this patent is extended or adjusted under 35 U.S.C. 154(b) by 194 days.

(21) Appl. No.: 14/604,368

(22) Filed: Jan. 23, 2015

(65) Prior Publication Data

US 2015/0133910 A1    May 14, 2015

Related U.S. Application Data

(63) Continuation of application No. 13/020,562, filed on Feb. 3, 2011, now Pat. No. 8,974,450.

(51) Int. Cl.
*A61B 18/18* (2006.01)
*A61B 18/00* (2006.01)
*A61B 90/00* (2016.01)

(52) U.S. Cl.
CPC .............. *A61B 18/1815* (2013.01); *A61B 2018/00577* (2013.01); *A61B 2018/00642* (2013.01);
(Continued)

(58) Field of Classification Search
CPC ............... A61B 18/18; A61B 18/1815; A61B 2018/00577; A61B 2018/00642;
(Continued)

(56) References Cited

U.S. PATENT DOCUMENTS

D223,367 S    4/1972 Kountz
D263,020 S    2/1982 Rau, III
(Continued)

FOREIGN PATENT DOCUMENTS

CN    1103807 A    6/1995
DE    390937 C    3/1924
(Continued)

OTHER PUBLICATIONS

Japanese Notice of Reasons for Rejection with English translation, dated Sep. 1, 2015, corresponding to Japanese Patent Application No. 2012-010935, 6 total pages, including English translation.
(Continued)

*Primary Examiner* — Michael Peffley
*Assistant Examiner* — Khadijeh Vahdat

(57) ABSTRACT

A microwave ablation system includes an antenna assembly configured to deliver microwave energy from a power source to tissue. One or more electrodes are disposed on the antenna assembly and are configured to be positioned relative to tissue upon insertion of the antenna assembly into tissue. The one or more electrodes are configured to generate a feedback signal in response to an electrical signal supplied thereto from the power source. The feedback signal corresponds to the proximity of tissue relative to the at least one electrode and is configured to be compared to a predetermined parameter to determine a depth of the insertion of the antenna assembly into tissue. The power source is configured to control the delivery of microwave energy to the antenna assembly based on the comparison.

17 Claims, 5 Drawing Sheets

(52) U.S. Cl.
CPC .............. *A61B 2018/00702* (2013.01); *A61B 2018/00875* (2013.01); *A61B 2018/1823* (2013.01); *A61B 2018/1838* (2013.01); *A61B 2018/1869* (2013.01); *A61B 2090/062* (2016.02)

(58) Field of Classification Search
CPC ........... A61B 2018/00702; A61B 2018/00875; A61B 2018/1823; A61B 2018/1838; A61B 2018/1869
USPC ..................................................... 606/33–50
See application file for complete search history.

(56) References Cited

U.S. PATENT DOCUMENTS

| | | | |
|---|---|---|---|
| D266,842 | S | 11/1982 | Villers et al. |
| D278,306 | S | 4/1985 | McIntosh |
| D295,893 | S | 5/1988 | Sharkany et al. |
| D295,894 | S | 5/1988 | Sharkany et al. |
| 5,341,807 | A | 8/1994 | Nardella |
| D354,218 | S | 1/1995 | Van de Peer |
| 5,957,922 | A | 9/1999 | Imran |
| D424,693 | S | 5/2000 | Pruter |
| D424,694 | S | 5/2000 | Tetzlaff et al. |
| D425,201 | S | 5/2000 | Tetzlaff et al. |
| 6,123,702 | A | 9/2000 | Swanson et al. |
| D449,886 | S | 10/2001 | Tetzlaff et al. |
| D457,958 | S | 5/2002 | Dycus et al. |
| D457,959 | S | 5/2002 | Tetzlaff et al. |
| 6,391,005 | B1 | 5/2002 | Lum et al. |
| 6,391,024 | B1 | 5/2002 | Sun et al. |
| D487,039 | S | 2/2004 | Webster et al. |
| D496,997 | S | 10/2004 | Dycus et al. |
| D499,181 | S | 11/2004 | Dycus et al. |
| D525,361 | S | 7/2006 | Hushka |
| D531,311 | S | 10/2006 | Guerra et al. |
| D533,942 | S | 12/2006 | Kerr et al. |
| D535,027 | S | 1/2007 | James et al. |
| D541,418 | S | 4/2007 | Schechter et al. |
| D541,938 | S | 5/2007 | Kerr et al |
| D564,662 | S | 3/2008 | Moses et al. |
| D576,932 | S | 9/2008 | Strehler |
| D594,736 | S | 6/2009 | Esjunin |
| D594,737 | S | 6/2009 | Kelly et al. |
| 7,580,743 | B2 | 8/2009 | Bourlion et al. |
| D606,203 | S | 12/2009 | Husheer et al. |
| D613,412 | S | 4/2010 | DeCarlo |
| D634,010 | S | 3/2011 | DeCarlo |
| 7,909,777 | B2 | 3/2011 | Freeman et al. |
| 7,938,787 | B2 | 5/2011 | Freeman et al. |
| 8,974,450 | B2 | 3/2015 | Brannan |
| 2001/0003798 | A1 | 6/2001 | McGovern et al. |
| 2003/0088242 | A1* | 5/2003 | Prakash ................. A61B 18/18 606/33 |
| 2005/0075629 | A1* | 4/2005 | Chapelon ............. A61B 5/0537 606/41 |
| 2007/0088417 | A1 | 4/2007 | Schouenborg |
| 2008/0033356 | A1 | 2/2008 | Kluge et al. |
| 2009/0012513 | A1 | 1/2009 | Utley et al. |
| 2010/0125269 | A1 | 5/2010 | Emmons et al. |
| 2010/0217253 | A1* | 8/2010 | Mehta ................. A61B 18/1477 606/33 |
| 2010/0228242 | A1 | 9/2010 | Wiksell et al. |
| 2010/0262135 | A1 | 10/2010 | Berube |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| EP | 0 246 350 A1 | 11/1987 |
| EP | 0 521 264 A2 | 1/1993 |
| EP | 0 556 705 A1 | 8/1993 |
| EP | 0 558 429 A1 | 9/1993 |
| EP | 0 648 515 A1 | 4/1995 |
| EP | 0 836 868 A2 | 4/1998 |
| EP | 0 882 955 A1 | 12/1998 |
| EP | 1 159 926 A2 | 12/2001 |
| EP | 2366352 A1 | 9/2011 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 5-5106 | 1/1993 |
| JP | 05-40112 | 2/1993 |
| JP | 06343644 A | 12/1994 |
| JP | 07265328 A | 10/1995 |
| JP | 08056955 A | 3/1996 |
| JP | H08-505544 A | 6/1996 |
| JP | 08252263 A | 10/1996 |
| JP | 09000492 A | 1/1997 |
| JP | 09010223 A | 1/1997 |
| JP | 11244298 A | 9/1999 |
| JP | H11-309124 A | 11/1999 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001037775 A | 2/2001 |
| JP | 2001128990 A | 5/2001 |
| JP | 2001231870 A | 8/2001 |
| JP | 2005525150 A | 8/2005 |
| JP | 2008142467 A | 6/2008 |
| SU | 166452 | 11/1964 |
| SU | 401367 A1 | 10/1973 |

(56) References Cited

FOREIGN PATENT DOCUMENTS

| SU | 727201 A2 | 4/1980 |
|---|---|---|
| WO | 2009094422 A1 | 7/2009 |
| WO | 2010/035831 A1 | 4/2010 |

OTHER PUBLICATIONS

U.S. Appl. No. 13/029,594, filed Feb. 17, 2011, Joseph D. Brannan.
U.S. Appl. No. 13/043,665, filed Mar. 9, 2011, Richard A. Willyard.
U.S. Appl. No. 13/043,694, filed Mar. 9, 2011, Richard A. Willyard.
U.S. Appl. No. 13/050,729, filed Mar. 17, 2011, Casey M. Ladtkow.
U.S. Appl. No. 13/083,185, filed Apr. 8, 2011, Arnold V. DeCarlo.
U.S. Appl. No. 13/083,256, filed Apr. 8, 2011, Joseph D. Brannan.
U.S. Appl. No. 13/098,199, filed Apr. 29, 2011, Roop L. Mahajan.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.TM. Breast Lesion Needle/ Wire Localizer, Namic.RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one p., Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. T Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyms PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.

Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure.TM." Diseases of the Colon & Rectum, vol. 46, No. 1, Jan. 2003.
Cosman et al., "Methods of Making Nervous System Lesions" in William RH, Rengachary SS (eds): Neurosurgery, New York: McGraw.cndot.Hill, vol. 111, (1984), pp. 2490-2499.
Cosman et al., "Radiofrequency Lesion Generation and its Effect on Tissue Impedance", Applied Neurophysiology, 51:230-242, 1988.
Cosman et al., Theoretical Aspects of "Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure.TM. Vessel Sealing System: A Case Report" Innovations That Work, Feb. 2002.
Humphries Jr. et al., "Finite.cndot.Element Codes to Model Electrical Heating and Non-Linear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure.TM. Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure.TM. Vessel Sealing System in Hemorrhoidectormy" American College of Surgeons (ACS) Clinic La Congress Poster (2000).
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.

(56) References Cited

OTHER PUBLICATIONS

European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004974.5 dated Apr. 6, 2011.
European Search Report EP 08004975 dated Jul. 24, 2008.
European Search Report EP 08006731.7 dated Jul. 29, 2008.
European Search Report EP 08006733 dated Jul. 7, 2008.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.
W. Scott Helton, "LigaSure.TM. Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 08006734.1 dated Aug. 18, 2008.
European Search Report EP 08006735.8 dated Jan. 8, 2009.
European Search Report EP 08007924.7 dated Aug. 17, 2010.
European Search Report EP 08011282 dated Aug. 14, 2009.
European Search Report EP 08011705 dated Aug. 20, 2009.
European Search Report EP 08011705.4 dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 dated Nov. 13, 2009.
European Search Report EP 09010877.0 dated Dec. 3, 2009.
European Search Report EP 09012389.4 dated Jul. 6, 2010.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 dated Oct. 30, 2009.
European Search Report EP 09165976.3 dated Mar. 17, 2010.
European Search Report EP 09166708 dated Oct. 15, 2009.
European Search Report EP 09166708.9 dated Mar. 18, 2010.
European Search Report EP 09169376.2 dated Dec. 16, 2009.
European Search Report EP 09172188.6 dated Apr. 23, 2010.
European Search Report EP 09172838.6 dated Jan. 20, 2010.
European Search Report EP 09173268.5 dated Jan. 27, 2010.
European Search Report EP 10001767.2 dated Jun. 18, 2010.
European Search Report EP 10004950.1 dated Jul. 2, 2010.

(56) References Cited

OTHER PUBLICATIONS

European Search Report EP 10004951.9 dated Jul. 2, 2010.
European Search Report EP 10005533.4 dated Sep. 24, 2010.
European Search Report EP 10005534.2 dated Sep. 17, 2010.
European Search Report EP 10006373.4 dated Nov. 11, 2010.
European Search Report EP 10008139.7 dated Nov. 30, 2010.
European Search Report EP 10008140.5 dated Dec. 28, 2010.
European Search Report EP 10008850.9 dated Nov. 30, 2010.
European Search Report EP 10009731.0 dated Jan. 28, 2011.
European Search Report EP 10009732.8 dated Jan. 26, 2011.
European Search Report EP 10010943.8 dated Feb. 1, 2011.
European Search Report EP 10011750.6 dated Feb. 1, 2011.
European Search Report EP 10014042.5 dated Feb. 18, 2011.
European Search Report EP 10158944.8 dated Jun. 21, 2010.
European Search Report EP 10161722.3 dated Jun. 16, 2010.
European Search Report EP 10163235.4 dated Aug. 10, 2010.
European Search Report EP 10185413.1 dated Dec. 7, 2010.
European Search Report EP 10185413.1 dated Mar. 14, 2011.
European Search Report EP 10191321.8 dated Apr. 7, 2011.
International Search Report PCT/US97/05066 dated Jun. 24, 1997.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
Johnson et al., "New Low-Profile Applicators for Local Heating of Tissues", IEEE Transactions on Biomedical Engineering, vol., BME-31, No. 1, Jan. 1984, pp. 28-37.
Johnson, "Use of the LigaSure.TM. Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure.TM. System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure.TM. Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure.TM. Vessel Sealing System and LigaSure.TM. Atlas 20 cm Open Instrument" Innovations That Work, Jun. 2003.
Muller et al., "Extended Left Hemicolectomy Using the LigaSure.TM. Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences.cndot.Yingyong Kexue Xuebao, Shangha CN, vol. 23, No. 2:(2005.cndot.03); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.

(56) References Cited

OTHER PUBLICATIONS

T. Seki et al., (1994) "Ultrasonically Guided Percutaneous Microwave Coagulation Therapy for Small Hepatocellular Carcinoma," Cancer 74(3):817-825.
Urologix, Inc.—Medical Professionals: Targis.TM. Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation:'COA-COMP'" Neurosurgical Review 7:2-3 (1984) pp. 187-190.
European Search Report for European Application No. 12000334.8 dated Apr. 20, 2012.
European Search Report from Appl. No. EP 14154297.7 dated Apr. 30, 2014.
U.S. Appl. No. 12/619,323, filed Nov. 16, 2009, Arnold V. DeCarlo.
U.S. Appl. No. 12/619,462, filed Nov. 16, 2009, Casey M. Ladtkow.
U.S. Appl. No. 12/620,289, filed Nov. 17, 2009, Joseph D. Brannan.
U.S. Appl. No. 12/642,623, filed Dec. 18, 2009, Prakash Manley.
U.S. Appl. No. 12/686,726, filed Jan. 13, 2010, Joseph D. Brannan.
U.S. Appl. No. 12/692,856, filed Jan. 25, 2010, Joseph D. Brannan.
U.S. Appl. No. 12/696,671, filed Jan. 29, 2010, Steven Kim.
U.S. Appl. No. 12/696,966, filed Jan. 29, 2010, Steven Kim.
U.S. Appl. No. 12/701,030, filed Feb. 5, 2010, Francesca Rossetto.
U.S. Appl. No. 12/708,974, filed Feb. 19, 2010, Joseph D. Brannan.
U.S. Appl. No. 12/709,014, filed Feb. 19, 2010, Joseph D. Brannan.
U.S. Appl. No. 12/712,864, filed Feb. 25, 2010, Joseph D. Brannan.
U.S. Appl. No. 12/713,429, filed Feb. 26, 2010, Anthony C. Lee.
U.S. Appl. No. 12/713,515, filed Feb. 26, 2010, Anthony C. Lee.
U.S. Appl. No. 12/713,641, filed Feb. 26, 2010, Anthony C. Lee.
U.S. Appl. No. 12/719,657, filed Mar. 8, 2010, Mani N. Prakash.
U.S. Appl. No. 12/722,034, filed Mar. 11, 2010, Casey M. Ladtkow.
U.S. Appl. No. 12/731,367, filed Mar. 25, 2010, Joseph D. Brannan.
U.S. Appl. No. 12/732,508, filed Mar. 26, 2010, Steven Kim.
U.S. Appl. No. 12/732,521, filed Mar. 26, 2010, Steven Kim.
U.S. Appl. No. 12/772,675, filed May 3, 2010, Brian Shiu.
U.S. Appl. No. 12/777,984, filed May 11, 2010, Joseph D. Brannan.
U.S. Appl. No. 12/786,671, filed May 25, 2010, Richard A. Willyard.
U.S. Appl. No. 08/136,098, filed Oct. 14, 1993, Roger A. Stern.
U.S. Appl. No. 08/483,742, filed Jun. 7, 1995, Roger A. Stern.
U.S. Appl. No. 12/787,639, filed May 26, 2010, Mani N. Prakash.
U.S. Appl. No. 12/792,904, filed Jun. 3, 2010, Ronald J. Podhajsky.
U.S. Appl. No. 12/792,932, filed Jun. 3, 2010, Ronald J. Podhajsky.
U.S. Appl. No. 12/792,947, filed Jun. 3, 2010, Ronald J. Podhajsky.
U.S. Appl. No. 12/792,970, filed Jun. 3, 2010, Ronald J. Podhajsky.
U.S. Appl. No. 12/793,037, filed Jun. 3, 2010, Ronald J. Podhajsky.
U.S. Appl. No. 12/823,211, filed Jun. 25, 2010, Mani N. Prakash.
U.S. Appl. No. 12/826,897, filed Jun. 30, 2010, Brian Shiu.
U.S. Appl. No. 12/826,902, filed Jun. 30, 2010, Brian Shiu.
U.S. Appl. No. 12/837,820, filed Jul. 16, 2010, Joseph D. Brannan.
U.S. Appl. No. 12/839,023, filed Jul. 19, 2010, Ronald J. Podhajsky.
U.S. Appl. No. 12/861,333, filed Aug. 23, 2010, Joseph D. Brannan.
U.S. Appl. No. 12/944,951, filed Nov. 12, 2010, Joseph D. Brannan.
U.S. Appl. No. 12/977,390, filed Dec. 23, 2010, Joseph D. Brannan.
U.S. Appl. No. 12/977,415, filed Dec. 23, 2010, Joseph D. Brannan.
U.S. Appl. No. 12/985,124, filed Jan. 5, 2011, Joseph D. Brannan.
U.S. Appl. No. 12/985,136, filed Jan. 5, 2011, Joseph D. Brannan.
U.S. Appl. No. 12/985,155, filed Jan. 5, 2011, Joseph D. Brannan.
U.S. Appl. No. 12/985,179, filed Jan. 5, 2011, Joseph D. Brannan.
U.S. Appl. No. 13/020,562, filed Feb. 3, 2011, Joseph D. Brannan.
U.S. Appl. No. 13/020,664, filed Feb. 3, 2011, Kenlyn S. Bonn.
U.S. Appl. No. 13/024,041, filed Feb. 9, 2011, Joseph D. Brannan.
U.S. Appl. No. 13/029,521, filed Feb. 17, 2011, Joseph D. Brannan.
European Search Report, dated Jul. 20, 2016, corresponding to European Application No. 16157339.9; 6 pages.
Japanese Office Action (with English translation), dated Mar. 29, 2016, corresponding to Japanese Patent Application No. 2012-010935; 7 total pages.
Japanese Office Action (with English translation), dated Nov. 22, 2016, corresponding to Japanese Application No. 2012-010935; 7 total pages.

* cited by examiner

SYSTEM AND METHOD FOR ABLATION PROCEDURE MONITORING USING ELECTRODES

The present application is a continuation application of U.S. patent application Ser. No. 13/020,562, filed on Feb. 3, 2011, the entire contents of which are incorporated by reference herein.

BACKGROUND

1. Technical Field

The present disclosure relates to apparatus and methods for providing energy to tissue and, more particularly, to electromagnetic radiation delivery procedures utilizing ablation probes and methods of monitoring an ablation procedure using electrodes.

2. Discussion of Related Art

Treatment of certain diseases requires destruction of malignant tumors. Electromagnetic radiation can be used to heat and destroy tumor cells. Treatment may involve inserting ablation probes into tissues where cancerous tumors have been identified. Once the probes are positioned, electromagnetic energy is passed through the probes into surrounding tissue.

In the treatment of diseases such as cancer, certain types of cancer cells have been found to denature at elevated temperatures that are slightly lower than temperatures normally injurious to healthy cells. Known treatment methods, such as hyperthermia therapy, use electromagnetic radiation to heat diseased cells to temperatures above 41° C. while maintaining adjacent healthy cells below the temperature at which irreversible cell destruction occurs. These methods involve applying electromagnetic radiation to heat, ablate and/or coagulate tissue. Microwave energy is sometimes utilized to perform these methods. Other procedures utilizing electromagnetic radiation to heat tissue also include coagulation, cutting and/or ablation of tissue.

Electrosurgical devices utilizing electromagnetic radiation have been developed for a variety of uses and applications. A number of devices are available that can be used to provide high bursts of energy for short periods of time to achieve cutting and coagulative effects on various tissues. There are a number of different types of instruments that can be used to perform ablation procedures. Typically, microwave instruments for use in ablation procedures include a microwave generator, which functions as an energy source, and a microwave surgical instrument having an antenna assembly for directing the energy to the target tissue. The microwave generator and surgical instrument are typically operatively coupled by a cable assembly having a plurality of conductors for transmitting microwave energy from the generator to the instrument, and for communicating control, feedback and identification signals between the instrument and the generator.

Microwave energy is typically applied via antenna assemblies that can penetrate tissue. Several types of antenna assemblies are known, such as monopole and dipole antenna assemblies. In monopole and dipole antenna assemblies, microwave energy generally radiates perpendicularly away from the axis of the conductor. A monopole antenna assembly includes a single, elongated conductor that transmits microwave energy. A typical dipole antenna assembly has two elongated conductors, which are linearly aligned and positioned end-to-end relative to one another with an electrical insulator placed therebetween. Each conductor may be about ¼ of the length of a wavelength of the microwave energy, making the aggregate length of the two conductors about ½ of the wavelength of the supplied microwave energy. During certain procedures, it can be difficult to assess the extent to which the microwave energy radiates into the surrounding tissue, making it difficult to determine the area or volume of surrounding tissue that will be or is ablated.

During operation, microwave antenna assemblies radiate microwave fields that, when the antenna assembly is used properly, are used therapeutically. However, when a microwave antenna assembly is not used properly, the radiated microwave fields may pose a hazard to both the patient and the user of the antenna assembly. Improper use of an antenna assembly, for example, may include insufficient insertion depth of the shaft of the antenna assembly into tissue. In this scenario, if the antenna assembly is not inserted to the minimum depth required for proper operation, microwave fields may undesirably propagate along the shaft toward the user.

SUMMARY

According to an embodiment of the present disclosure, a microwave ablation system includes an antenna assembly configured to deliver microwave energy from a power source to tissue. One or more electrodes are disposed on the antenna assembly and are configured to be positioned relative to tissue upon insertion of the antenna assembly into tissue. The one or more electrodes are configured to generate a feedback signal in response to an electrical signal supplied thereto from the power source. The feedback signal corresponds to the proximity of tissue relative to the at least one electrode and is configured to be compared to a predetermined parameter to determine a depth of the insertion of the antenna assembly into tissue. The power source is configured to control the delivery of microwave energy to the antenna assembly based on the comparison.

According to another embodiment of the present disclosure, a method of performing a tissue ablation procedure includes the steps of inserting an antenna assembly into tissue and generating an electrical signal from a power source to at least one electrode disposed on the antenna assembly. The method also includes the step of generating a feedback signal in response to the electrical signal. The feedback signal depends on the proximity of tissue relative to the at least one electrode. The method also includes the steps of comparing the feedback signal to a predetermined parameter and determining an insertion depth of the antenna assembly relative to tissue based on the comparison. The method also includes the step of controlling delivery of energy from the power source to the antenna assembly for application to tissue based on the comparison.

According to another embodiment of the present disclosure, a microwave antenna assembly includes an antenna configured to deliver microwave energy to tissue. The antenna includes an inner conductor, an outer conductor and an inner insulator disposed therebetween. One or more electrodes are disposed on the antenna and are configured to be positioned relative to tissue upon insertion of the antenna into tissue. The one or more electrodes are configured to receive an electrical signal and generate a feedback signal in response to the received signal. The feedback signal corresponds to the proximity of tissue relative to the at least one electrode and the feedback signal is configured to be compared to one or more predetermined parameters to determine a depth of the insertion of the antenna into tissue. The delivery of microwave energy from the antenna to tissue is based on the comparison.

DETAILED DESCRIPTION

Figure 1:
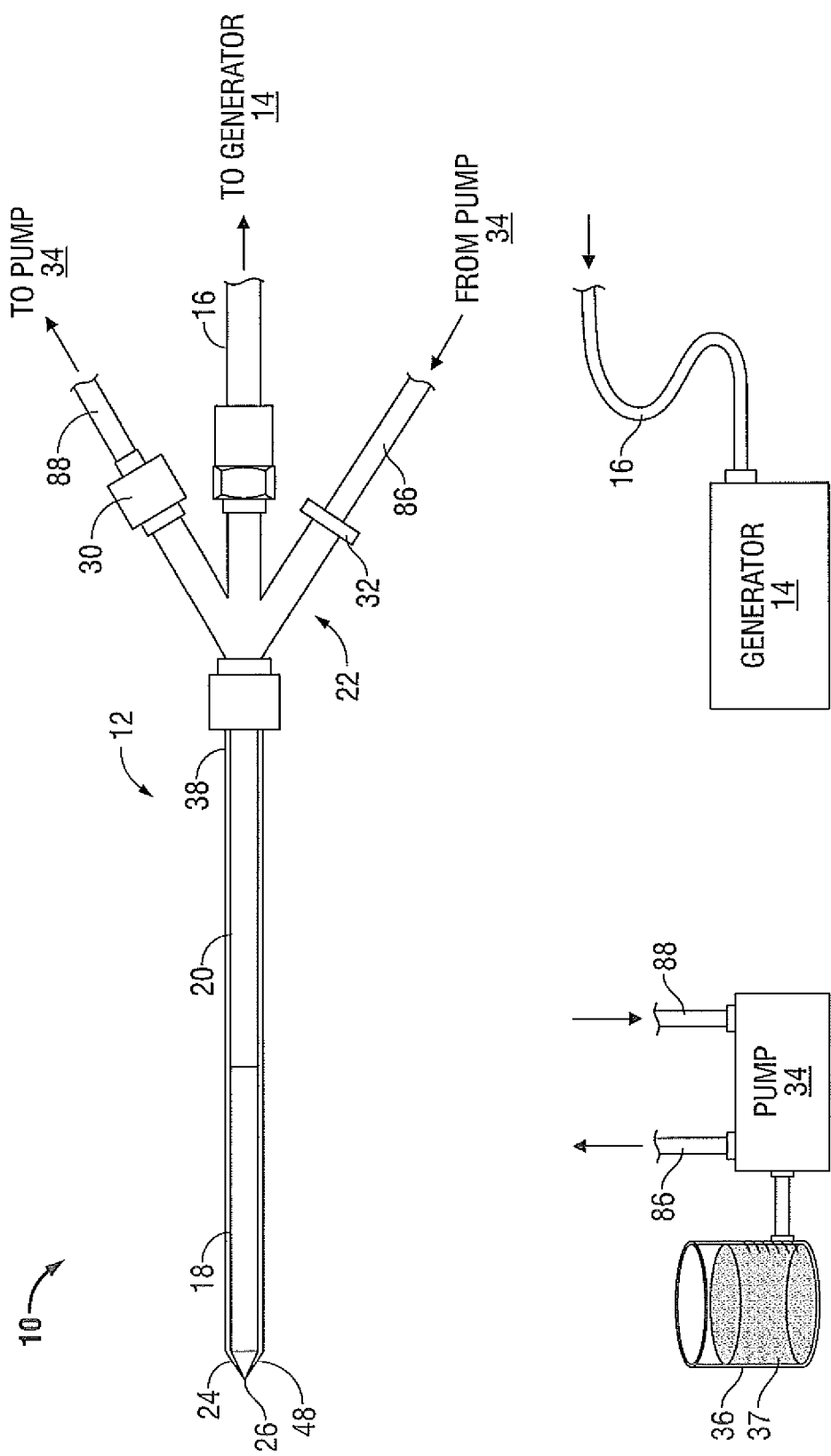
FIG. 1 shows a diagram of a microwave antenna assembly in accordance with an embodiment of the present disclosure.

Embodiments of the presently disclosed apparatus are described in detail below with reference to the drawings wherein like reference numerals identify similar or identical elements in each of the several views. In the discussion that follows, the term "proximal" will refer to the portion of a structure that is closer to a user, while the term "distal" will refer to the portion of the structure that is farther from the user.

Generally, the present disclosure is directed to a microwave antenna assembly having an energy source or generator adapted to deliver energy to tissue via the antenna assembly. More particularly, the present disclosure is directed to monitoring insertion depth of the microwave antenna assembly into tissue and controlling the delivery of energy from the energy source based on the monitored insertion depth.

In some embodiments, two or more bipolar electrodes are operably coupled to the antenna assembly and an associated energy source. The energy source supplies electrical energy (e.g., RF energy) to each bipolar electrode in a bipolar manner to elicit a measurable response (e.g., impedance, capacitance, inductance, etc.) that varies depending on whether tissue is present at or between the bipolar electrodes. As such, the bipolar electrodes may be strategically disposed on the antenna assembly at a predetermined location such that as the antenna assembly travels distally into tissue and, likewise, as tissue travels proximally along the longitudinal length of the antenna assembly to reach the proximity of the bipolar electrodes, the elicited response at the bipolar electrodes detectably changes relative to when tissue is absent from the proximity of the bipolar electrodes. The difference in the elicited response between the presence and non-presence of tissue at or between the bipolar electrodes is detected by the energy source and interpreted in accordance with predetermined data (e.g., a range of impedance values, capacitance values, and/or inductance values) to determine whether the insertion depth of the antenna assembly is adequate or inadequate. As explained in detail below, the output of the energy source (e.g., microwave energy) is controlled in accordance with this determination.

In some embodiments, one or more monopolar electrodes may be operably coupled to the antenna assembly and an associated energy source. The energy source supplies electrical energy (e.g., RF energy) to the monopolar electrode(s) in a monopolar manner to elicit a measurable response (e.g., impedance, capacitance, inductance, etc.) that varies depending on whether tissue is present at the monopolar electrode(s).

Hereinafter, embodiments of the presently disclosed tissue ablation systems are described with reference to the accompanying drawings. Like reference numerals may refer to similar or identical elements throughout the description of the figures. As used herein, the term "microwave" generally refers to electromagnetic waves in the frequency range of 300 megahertz (MHz) ($3 \times 10^8$ cycles/second) to 300 gigahertz (GHz) ($3 \times 10^{11}$ cycles/second). As used herein, the phrase "transmission line" generally refers to any transmission medium that can be used for the propagation of signals from one point to another.

Various embodiments of the present disclosure provide electrosurgical systems for treating tissue and methods of controlling the delivery of electromagnetic radiation to tissue. Embodiments may be implemented using electromagnetic radiation at microwave frequencies or at other frequencies. Electrosurgical systems for treating tissue, according to various embodiments of the present disclosure, deliver microwave power to a plurality of electrosurgical devices. Electrosurgical devices, such as ablation probes, for implementing embodiments of the present disclosure may be inserted directly into tissue, inserted through a lumen, such as a vein, needle or catheter, placed into the body during surgery by a clinician, or positioned in the body by other suitable methods.

FIG. 1 shows a microwave ablation system 10 that includes a microwave antenna assembly 12 coupled to a microwave generator 14 via a flexible coaxial cable 16. The generator 14 is configured to provide microwave energy at an operational frequency from about 300 MHz to about 10,000 MHz, although other suitable frequencies are also contemplated.

In the illustrated embodiment, the antenna assembly 12 includes a radiating portion 18 connected by feedline 20 (or shaft) to the cable 16. More specifically, the antenna assembly 12 is coupled to the cable 16 through a connection hub 22 having an outlet fluid port 30 and an inlet fluid port 32 that are connected in fluid communication with a sheath 38. The sheath 38 encloses radiating portion 18 and feedline 20 to form a chamber 89 (FIG. 2) allowing a coolant fluid 37 to circulate from port 32 around the antenna assembly 12 to port 30. The ports 30 and 32 are also coupled to a supply pump 34 via supply lines 88 and 86, respectively. Supply pump 34 is, in turn, fluidly coupled to a supply tank 36. The supply pump 34 may be a peristaltic pump or any other suitable type. The supply tank 36 stores the coolant fluid 37 and, in some embodiments, may maintain the fluid at a predetermined temperature. More specifically, the supply tank 36 may include a coolant unit that cools the returning liquid from the antenna assembly 12. In another embodiment, the coolant fluid 37 may be a gas and/or a mixture of fluid and gas.

Figure 2A:
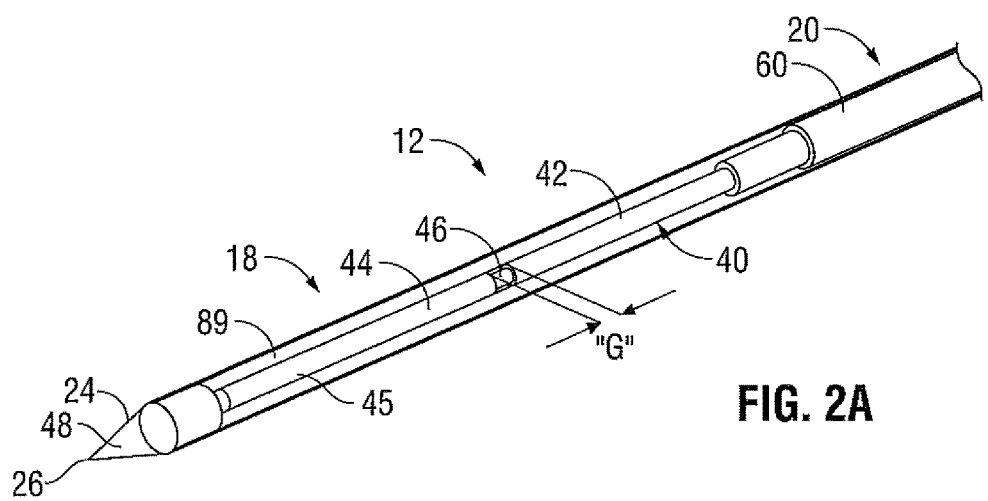
FIG. 2A shows a perspective view of a distal end of the microwave antenna assembly of FIG. 1.
Figure 2B:
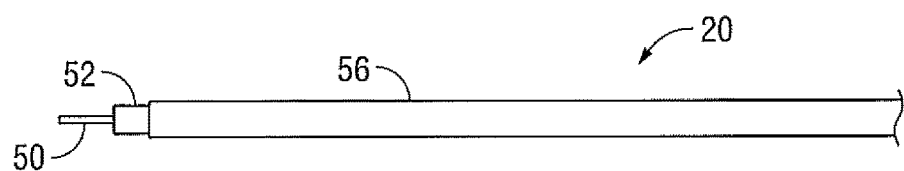
FIG. 2B shows a side view of a distal end of the microwave antenna assembly of FIG. 1.

FIGS. 2A and 2B illustrate the radiating portion 18 of the antenna assembly 12 having a dipole antenna 40. The dipole antenna 40 is coupled to the feedline 20 that electrically connects antenna assembly 12 to the generator 14. As shown in FIG. 2B, the feedline 20 includes an inner conductor 50 (e.g., wire) surrounded by an insulator 52 that is, in turn, surrounded by an outer conductor 56 (e.g., a cylindrical conducting sheath). The inner and outer conductors may be constructed of copper, gold, stainless steel, or other conductive metals with similar conductivity properties. The metals may be plated with other materials, for example, other conductive materials. In one embodiment, feedline 20 may be formed from a coaxial semi-rigid or flexible cable.

The dipole antenna 40 includes a proximal portion 42 and a distal portion 44 interconnected at a feed point 46. The distal portion 44 and the proximal portion 42 may be either balanced (e.g., of equal lengths) or unbalanced (e.g., of unequal lengths). A dipole feed gap "G" is disposed between the proximal and distal portions 42 and 44 at the feed point 46. The gap "G" may be from about 1 mm to about 3 mm. In one embodiment, the gap "G" may be thereafter filled with a dielectric material at the feed point 46. The dielectric material may be polytetrafluoroethylene (PTFE), such as Teflon® sold by DuPont of Willmington, Del. In another embodiment, the gap "G" may be coated with a dielectric seal coating.

The distal portion 44 includes a conductive member 45 that may be formed from any type of conductive material, such as metals (e.g., copper, stainless steel, tin, and various alloys thereof). The distal portion 44 may have a solid structure and may be formed from solid wire (e.g., 10 AWG).

With reference to FIG. 2A, the antenna assembly 12 also includes a choke 60 disposed around the feedline 20. The choke 60 may be a quarter-wavelength shorted choke that is shorted to the feedline 20 at the proximal end (not illustrated) of the choke 60 by soldering or other suitable methods.

With continued reference to FIG. 2A, antenna assembly 12 also includes a tip 48 having a tapered end 24 that terminates, in one embodiment, at a pointed end 26 to allow for insertion into tissue with minimal resistance at a distal end of the radiating portion 18. In those cases where the radiating portion 18 is inserted into a pre-existing opening, tip 48 may be rounded or flat. The tip 48 may be formed from a variety of heat-resistant materials suitable for penetrating tissue, such as metals (e.g., stainless steel), various thermoplastic materials (e.g., poletherimide and polyamide thermoplastic resins), and ceramics (e.g., partially stabilized zirconia).

Figure 3:
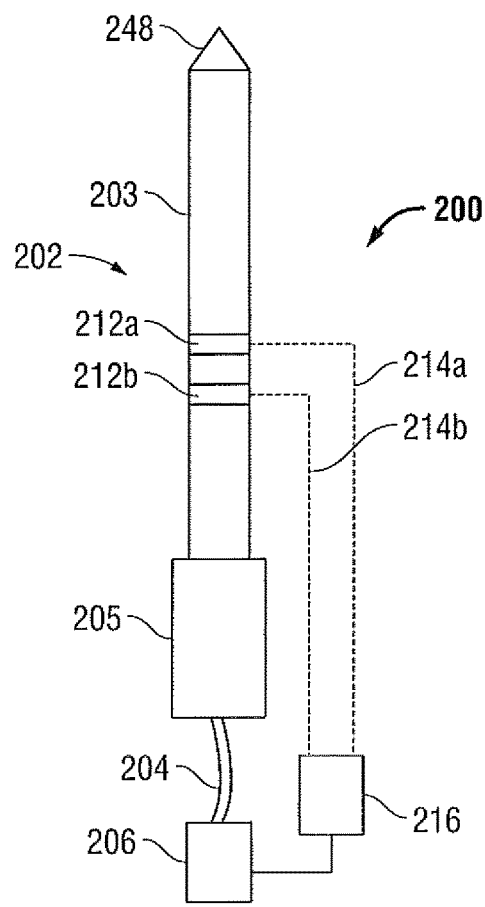
FIG. 3 shows a system block diagram of a microwave antenna assembly according to another embodiment of the present disclosure.

With reference to FIG. 3, a microwave ablation system, shown generally as 200, according to an embodiment of the present disclosure is depicted. The system 200 includes an ablation device 202 having a handle 205 and an antenna 203 used to ablate tissue. A microwave generator 206, which is substantially similar to generator 14 of FIG. 1, supplies the ablation device 202 with energy (e.g., microwave energy) via coaxial cable 204.

As shown in FIG. 3, a pair of electrodes 212a and 212b are disposed on the antenna 203 and operably coupled to a controller 216 via transmission lines 214a and 214b, respectively. Controller 216 may be operably coupled to the microwave generator 206, as illustrated in FIG. 3, or may be incorporated within the microwave generator 206 (not shown). Although not shown as such in FIG. 3, transmission lines 214a and 214b may extend proximally from electrodes 212a and 212b along an outer surface of the antenna 203 (e.g., via conductive tracing), and, further, through the handle 205 and cable 204 for connection to the generator 206 and/or controller 216. Electrodes 212a and 212b are electrically connected to the generator 206 such that generator 206 supplies electrosurgical energy (e.g., RF energy, microwave energy, etc.) to electrodes 212a and 212b in a bipolar configuration. More specifically, generator 206 generates energy at a first potential (e.g., "−") to one of the electrodes (e.g., 212a) and at a second potential (e.g., "+") to the other electrode (e.g., 212b). In this scenario, electrodes 212a, 212b are configured to conduct a suitable amount of electrosurgical energy therethrough such that a measurable response (e.g., impedance, capacitance, inductance, etc.) may be elicited from electrodes 212a, 212b caused by the proximity or lack of presence or lack of presence of tissue relative to the electrodes 212a, 212b. As described in more detail below, this measurable response varies depending on the proximity of tissue to the electrodes 212a, 212b. That is, the measurable response corresponding to the presence of tissue at or between the electrodes 212a, 212b is detectably different from the measurable response corresponding to the lack of presence of tissue at or between the electrodes 212a, 212b. It is this variation in the measureable response that is monitored by the controller 216 and/or generator 206 to determine whether the insertion depth of the antenna 203 relative to tissue is desired or appropriate. This determination is, in turn, utilized to control the delivery of energy from the generator 206 to the antenna 203.

When antenna 203 is not inserted into tissue to a sufficient depth, unintentional damage to surrounding tissue may occur. By monitoring the insertion depth of antenna 203 and controlling output of the generator 206 accordingly, that is, by applying energy to tissue only when antenna 203 is detected as being inserted into tissue at an appropriate depth, damage to the ablation system 200, the user, and/or the patient may be prevented. With this purpose in mind, controller 216 is configured to control the output of generator 206 based on an input signal received from one of or both of electrodes 212a and 212b in response to an electrical signal (e.g., RF energy) transmitted from generator 206 to electrodes 212a, 212b via transmission lines 214a, 214b, respectively. Controller 216 may be a microprocessor or any suitable logic circuit configured to receive and process an input signal from electrodes 212a and 212b and control output of generator 206 based on the processed input signal. Controller 216 may be operably coupled to a storage device or memory (not shown) configured to store programmable instructions, historical data, lookup tables, operating parameters, etc.

By placing electrodes 212a and 212b at predetermined locations along the longitudinal length of antenna 203 and relative to each other, impedance measurements of electrodes 212a and 212b may be utilized to monitor the insertion depth of antenna 203 relative to tissue. More specifically, the impedance of electrodes 212a and 212b when no tissue is present at or between electrodes 212a and 212b (e.g., antenna 203 is not inserted into tissue at a depth sufficient to cause tissue to be disposed at or between electrodes 212a, 212b) is detectably different than the impedance of electrodes 212a and 212b when tissue is present at or between electrodes 212a and 212b (e.g., antenna 203 is inserted into tissue at a depth sufficient to cause tissue to be disposed at or between electrodes 212a, 212b). In this manner, the detected impedance of electrodes 212a and 212b may be processed by the controller 216 to detect sufficient insertion depth of antenna 203 relative to tissue and, in turn, control output of generator 206 accordingly. For example, controller 216 may prevent generator 206 from supplying energy to the ablation device 202 until the antenna 203 is inserted into tissue at a sufficient depth for proper operation of device 202.

In some embodiments, one or more sensors (not shown) may be in operative communication with electrodes 212a, 212b and configured to provide real-time information pertaining to electrodes 212a, 212b to the generator 206 and/or the controller 216 via suitable transmission lines. More particularly, these sensors may be configured to provide real-time information pertaining to one or more electrical parameters (e.g., impedance, power, voltage, current, etc.), thermal parameters (e.g., temperature), etc., associated with the electrodes 212a, 212b. In some embodiments, the sensors may be in the form of a thermal sensor such as, for example, a thermocouple, a thermistor, an optical fiber, etc.

The sufficient insertion depth and/or the placement of electrodes 212a and 212b on the antenna 203 may be pre-measured and/or predetermined based on any suitable parameter such as, for example without limitation, electrode geometry, electrode spacing, antenna geometry, antenna length, a manufacturer suggested minimum insertion depth, and/or a predetermined range of sufficient insertion depths.

As discussed in further detail below, electrodes 212a, 212b may be configured in any number of geometries and/or lateral spacing configurations in accordance with the type of elicited response being detected to determine insertion depth. In particular, impedance measurements such as resistance and capacitance may predetermine the lateral or circumferential spacing between electrodes 212a, 212b as well as the geometry thereof for purposes of improving the resolution between elicited responses corresponding to the presence and lack of presence of tissue, thereby optimizing the detection of insertion depth and the overall operation of system 200.

In use, an electrical signal (e.g., RE energy) is generated by generator 206 and transmitted to electrodes 212a and 212b. In response, electrodes 212a, 212b provide an electrical feedback signal to the controller 216 that represents a real-time measurement or indication of one or more parameters pertaining to electrodes 212a, 212b such as impedance (e.g., capacitance, resistance, etc.). Controller 216 compares the electrical signal to a predetermined range. If the electrical signal is within the predetermined range, for example, indicating that antenna 203 is inserted into tissue at an appropriate depth, the controller 216 controls the generator 206 to supply energy to the antenna 203 for application to tissue. That is, the appropriate insertion depth of antenna 203 may be determined prior to an ablation procedure being performed such that the supply of energy to device 202 may be initiated and/or in real-time during an ablation procedure such that the application of energy to tissue may be continued. If the electrical signal is outside the predetermined range, for example, indicating that the antenna 203 is not inserted into tissue at an appropriate depth, the controller 216 controls the generator 206 to modify or terminate generator 206 output. That is, if prior to the ablation procedure being performed it is determined that antenna 203 is not inserted into tissue at an appropriate depth, controller 216 controls generator 206 to prevent the supply of energy to device 202. Likewise, if during the ablation procedure it is determined that antenna 203 is not inserted into tissue at an appropriate depth, controller 216 controls generator 206 to terminate the supply of energy to device 202. In this way, generator 206 will supply energy to antenna 203 for application to tissue only when antenna 203 is inserted into tissue at an appropriate depth as determined by the methods described hereinabove. The predetermined range may be, for example, a predetermined range of impedance values.

Each of electrodes 212a and 212b may be disposed anywhere along the longitudinal length of antenna 203, e.g., proximal to the radiating portion 18 (FIG. 1), and may be laterally spaced at a suitable distance from each other such that system 200 is optimized for detecting insertion depth of the antenna 203.

As described hereinabove, electrodes 212a, 212b may be configured in any number of geometries and/or lateral spacing configurations in accordance with the type of parameter being detected to determine insertion depth. FIGS. 4A-8 illustrate various embodiments of the ablation device 202 including bipolar electrodes that operate in conjunction with system 200 substantially as described above with respect to electrodes 212a, 212b to enable the detection of insertion depth of antenna 203, and are described in detail below.

Figure 4A:
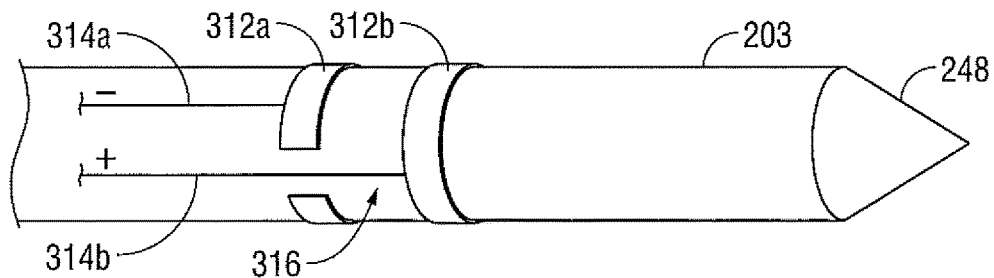
FIG. 4A shows a distal end of the microwave antenna assembly of FIG. 3 according to another embodiment of the present disclosure.
Figure 4B:
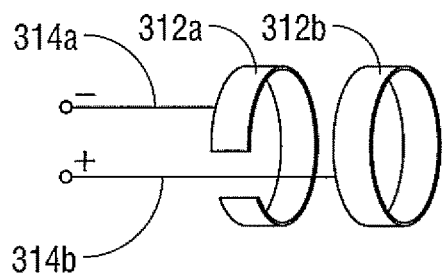
FIG. 4B shows a pair of electrodes separated from the microwave antenna assembly of FIG. 4A.

With reference to FIG. 4A, a pair of laterally spaced ring electrodes 312a, 312b is shown operably coupled to the antenna 203 in accordance with some embodiments of the present disclosure. Electrodes 312a and 312b are configured to operate in conjunction with microwave ablation system 200 as substantially described above with reference to electrodes 212a and 212b. Electrodes 312a and 312b are electrically connected to generator 206 and/or controller 216 (FIG. 3) via transmission lines 314a and 314b, respectively, and include a lateral space 316 disposed therebetween. FIG. 4B shows the pair of electrodes 312a, 312b separated from antenna 203 to illustrate that electrode 312a is generally c-shaped. In this way, when electrode 312a is operably coupled to antenna 203, electrode 312a does not completely encompass the circumference of antenna 203 such that transmission line 314b is enabled to extend proximally along an outer surface of antenna 203 without interference from electrode 312a, as illustrated in FIG. 4A. In use, when tissue is disposed within the lateral spacing 316 disposed between electrodes 312a and 312b, the impedance of electrodes 312a and 312b detectably changes from when there is air and/or no tissue disposed within the space 316.

Figure 5A:
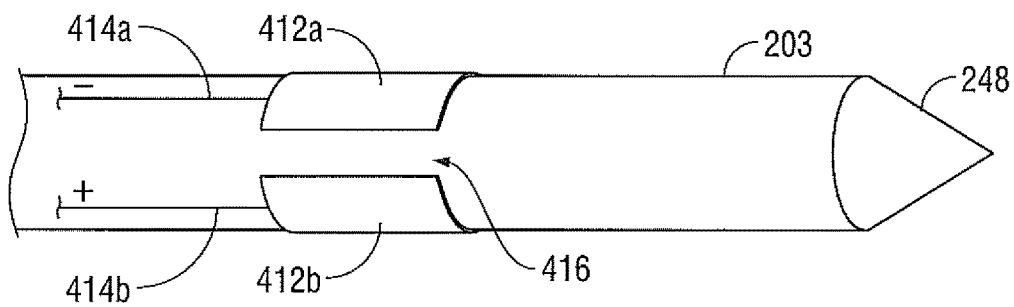
FIG. 5A shows a distal end of the microwave antenna assembly of FIG. 3 according to another embodiment of the present disclosure.
Figure 5B:
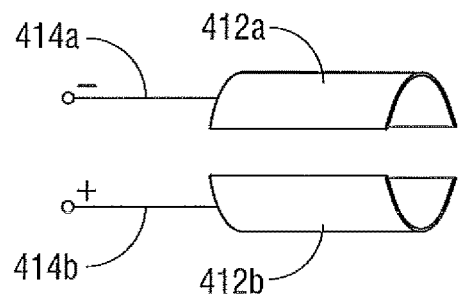
FIG. 5B shows a pair of electrodes separated from the microwave antenna assembly of FIG. 5A.

With reference to FIG. 5A, a pair of electrodes 412a, 412b is shown operably coupled to antenna 203 in accordance with some embodiments of the present disclosure. Electrodes 412a and 412b are configured to operate in conjunction with microwave ablation system 200 as substantially described above with reference to electrodes 212a and 212b. Electrodes 412a and 412b are electrically connected to generator 206 and/or controller 216 (FIG. 3) via transmission lines 414a and 414b, respectively. FIG. 5B shows the pair of electrodes 412a and 412b separated from antenna 203 to illustrate that electrodes 412a, 412b are generally c-shaped or half-cylinder in shape. In this way, when electrodes 412a, 412b are operably coupled to antenna 203, electrodes 412a, 412b do not completely encompass the circumference of antenna 203 such that a space 416 is defined therebetween. In use, when tissue is disposed within the space 416 between electrodes 412a, 412b, the impedance of electrodes 412a, 412b delectably changes from when there is air and/or no tissue disposed within the space 416.

Figure 6A:
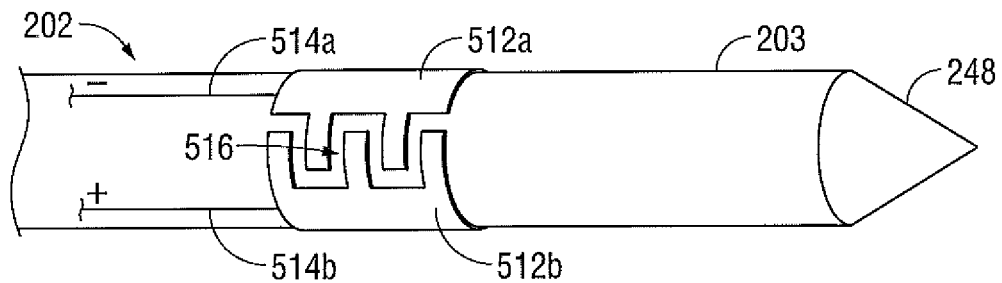
FIG. 6A shows a distal end of the microwave antenna assembly of FIG. 3 according to another embodiment of the present disclosure.
Figure 6B:
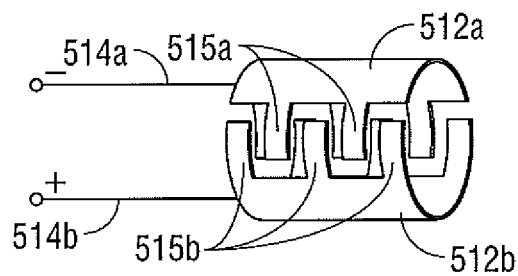
FIG. 6B shows a pair of electrodes separated from the microwave antenna assembly of FIG. 6A.

With reference to FIG. 6A, a pair of electrodes 512a, 512b is shown operably coupled to antenna 203 in accordance with some embodiments of the present disclosure. Electrodes 512a and 512b are configured to operate in conjunction with microwave ablation system 200 as substantially described above with reference to electrodes 212a and 212b. Electrodes 512a and 512b are electrically connected to generator 206 and/or controller 216 (FIG. 3) via transmission lines 514a and 514b, respectively. FIG. 6B shows the pair of electrodes 512a, 512b separated from antenna 203 to illustrate that electrodes 512a, 512b are generally c-shaped. Electrodes 512a and 512b include a plurality of laterally spaced interlocking fingers 515a and 515b, respectively, that define a spacing 516 between electrodes 512a, 512b. In operation, this interlocking or nested configuration operates to increase capacitance between electrodes 512a, 512b due to the close proximity of the fingers 515a and 515b. In this way, the resolution between elicited responses—namely, capacitance in the present scenario—corresponding to the presence and lack of presence of tissue within spacing 516 is improved, thereby optimizing the detection of insertion depth and the overall operation of system 200.

Figure 7A:
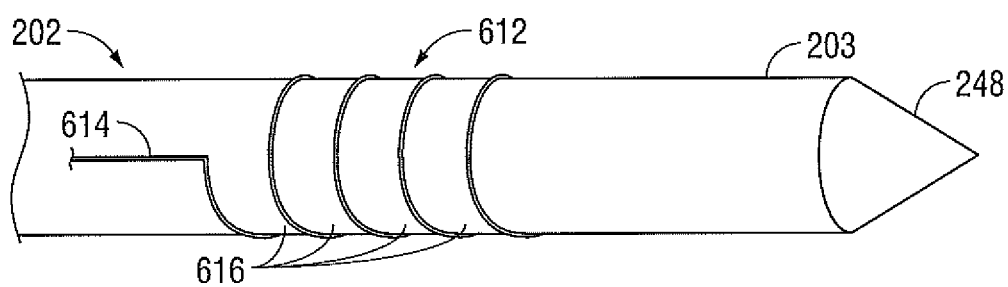
FIG. 7A shows a distal end of the microwave antenna assembly of FIG. 3 according to another embodiment of the present disclosure.
Figure 7B:
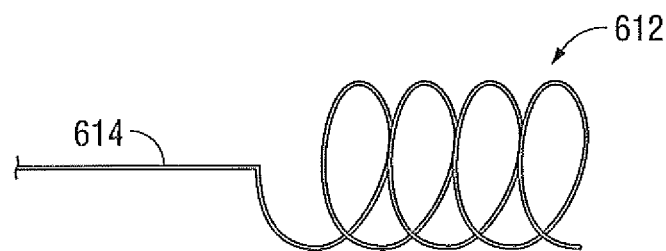
FIG. 7B shows an electrode separated from the microwave antenna assembly of FIG. 7A.

With reference to FIG. 7A, a monopolar coil electrode 612 is shown operably coupled to antenna 203 in accordance with some embodiments of the present disclosure. Electrode 612 is configured to operate in conjunction with microwave ablation system 200. Electrode 612 is electrically connected to generator 206 and/or controller 216 (FIG. 3) via a transmission line 614. Generator 206 generates energy at a single potential (e.g., either "+" or "−") to electrode 612. In this scenario, a return electrode or return pad attached to the patient may be utilized to return the energy to the generator 206, thereby completing the circuit following from the generator 206 to the antenna 203 for application to tissue and, subsequently, back to the generator 206. FIG. 7B shows the electrode 612 separated from antenna 203 to illustrate that electrode 612 is generally helical in shape such that the electrode 612 completely encircles the circumference of antenna 203 along at least a portion of the antenna's 203 longitudinal length.

As shown in FIG. 7A, the windings of the electrode 612 define lateral spacing 616 therebetween along at least a portion of the longitudinal length of the antenna 203. Similar to electrodes 512a, 512b shown in FIGS. 6A and 6B, in operation, the helical configuration of electrode 612 operates to increase the electrode's 612 capacitance due to the close proximity of the helical windings thereof. In this way, the resolution between elicited responses—namely, capacitance in the present scenario—corresponding to the presence and lack of presence of tissue within spacing 616 is improved, thereby optimizing the detection of insertion depth and the overall operation of system 200.

Figure 8A:
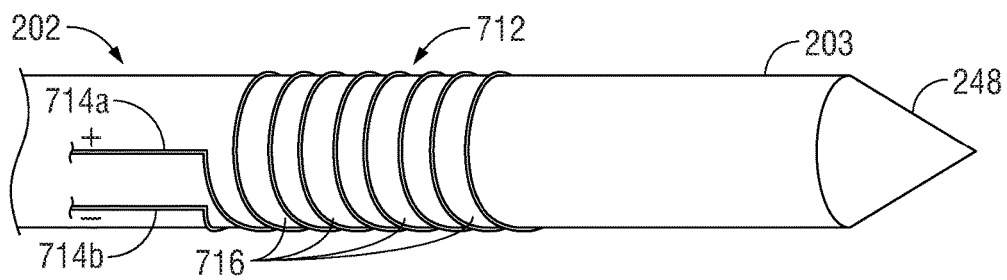
FIG. 8A shows a distal end of the microwave antenna assembly of FIG. 3 according to another embodiment of the present disclosure.
Figure 8B:
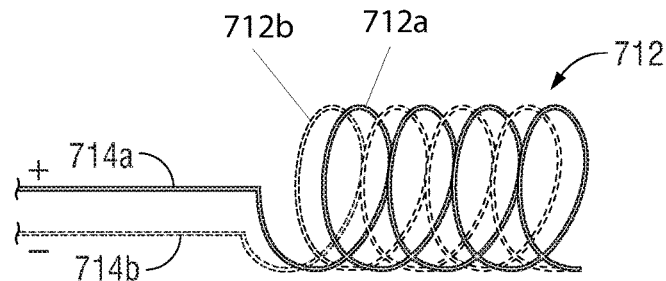
FIG. 8B shows a pair of electrodes separated from the microwave antenna assembly of FIG. 8A.

With reference to FIG. 8A, a pair of bipolar coil electrodes 712 is shown operably coupled to antenna 203 in accordance with some embodiments of the present disclosure. The pair of bipolar coil electrodes 712 includes a first electrode 712a and a second electrode 712b each configured to operate in conjunction with microwave ablation system 200. Electrodes 712a, 712b are electrically connected to generator 206 and/or controller 216 (FIG. 3) via transmission lines 714a, 714b, respectively. Generator 206 generates energy at a first potential (e.g., "+") to electrode 712a and at a second potential (e.g., "−") to electrode 712b. FIG. 8B shows the pair of electrodes 712a, 712b separated from antenna 203 to illustrate that electrodes 712a, 712b are generally helical in shape.

As shown in FIG. 8A, the generally helical-shaped electrodes 712a, 712b completely encircle the circumference of antenna 203 along at least a portion of the antenna's 203 longitudinal length such that the windings of electrodes 712a, 712b are intertwined to define lateral spacing 716 therebetween. Similar to electrodes 512a, 512b shown in FIGS. 6A and 6B, in operation, the helical configuration of electrodes 712a, 712b operates to increase the capacitance of electrodes 712a, 712b due to the close proximity of the intertwined helical windings thereof. In this way, the resolution between elicited responses—namely, capacitance in the present scenario—corresponding to the presence and lack of presence of tissue within spacing 716 is improved, thereby optimizing the detection of insertion depth and the overall operation of system 200.

Figure 9:
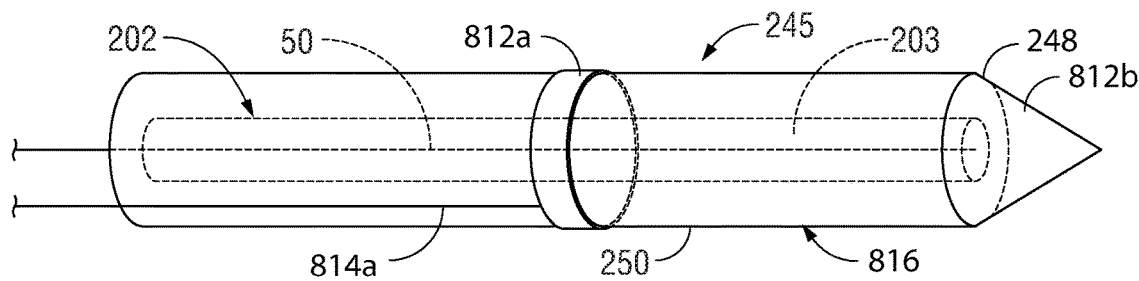
FIG. 9 shows a distal end of the microwave antenna assembly of FIG. 3 according to another embodiment of the present disclosure.

With reference to FIG. 9, the antenna 203, in some embodiments, may be operably associated with a trocar 245 that is configured to facilitate penetration into tissue for proper placement of the antenna 203 relative to a desired tissue site. The trocar 245 includes a hollow coaxial shaft 250 having a distal tip 248 disposed at a distal end thereof. The distal tip 248 has a generally tapered shape, e.g., conical, to facilitate the penetration thereof, and trocar 245 generally, into tissue. As shown in FIG. 9, the antenna 203 is configured to be accommodated within the hollow coaxial shaft 250 such that a distal end of the antenna 203 is operably coupled to the distal tip 248 of the trocar 245. In this scenario, the monitoring of insertion depth of antenna 203 into tissue may be accomplished by incorporating a pair of laterally spaced electrodes 812a and 812b disposed along the longitudinal length of the shaft 250. More specifically, and as shown by the illustrated embodiment of FIG. 9, electrode 812b forms the distal tip 248 of the trocar 245 and is electrically connected to generator 206 and/or controller 216 (FIG. 3) via the inner conductor 50 (also see FIG. 2B) of the antenna 203.

Electrode 812a is ring-like in shape and encircles the circumference of the shaft 250 of trocar 245 along at least a portion of the longitudinal length of the shaft 250. Electrode 812a is laterally spaced proximally from electrode 812b to define a space 816 therebetween. Electrode 812a is electrically connected to generator 206 and/or controller 216 (FIG. 3) via a transmission line 814a. As shown in the illustrated embodiment, transmission line 814a extends proximally from electrode 812a along an outer surface of the trocar 245. In some embodiments, although not shown, transmission line 814a may be connected through the shaft 250 to the outer conductor 56 (also see FIG. 2B) of the antenna 203. In this scenario, the outer conductor 56 would operate to electrically connect electrode 812a to the generator 206 and/or controller 216 (FIG. 3).

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An ablation device, comprising:
   an antenna having a proximal end portion and a distal end portion; and
   a trocar including:
   a shaft operably associated with the distal end portion of the antenna, the antenna extending longitudinally within the shaft;
   a first electrode disposed on a proximal end portion of the shaft; and
   a second electrode forming a distal tip of the shaft and configured for insertion into tissue, the proximal end portion of the shaft having a tubular outer surface formed with the distal tip, wherein the first and second electrodes are longitudinally spaced from one another along a longitudinal axis defined by the shaft.

2. The ablation device according to claim 1, wherein the distal end portion of the antenna is operably coupled to the distal tip of the trocar.

3. The ablation device according to claim 1, wherein the distal tip of the trocar is conical and configured to penetrate tissue.

4. The ablation device according to claim 1, wherein the first electrode is ring-like and at least partially encircles the shaft of the trocar.

5. The ablation device according to claim 1, wherein the antenna further includes an inner conductor electrically connected to the second electrode.

6. The ablation device according to claim 1, wherein the first electrode abuts the tubular outer surface of the proximal end portion of the shaft.

7. The ablation device according to claim 1, wherein the antenna has a distal end that terminates proximally of the second electrode.

8. The ablation device according to claim 1, wherein the tubular outer surface has a distal end directly connected to the distal tip.

9. An ablation system, comprising:
   an antenna having a proximal end portion and a distal end portion;
   a trocar including:
   a shaft defining a longitudinal axis therethrough and having a distal end portion operably associated with the distal end portion of the antenna;
   a first electrode disposed on a proximal end portion of the shaft; and
   a second electrode extending distally from the distal end portion of the shaft and configured for insertion into tissue, the proximal end portion of the shaft having a tubular outer surface formed with the second electrode, the first and second electrodes longitudinally spaced from one another along the longitudinal axis of the shaft;
   a power source electrically connected to at least one of the first electrode or the second electrode; and
   a controller operably associated with the power source, wherein the controller is configured to determine an insertion depth of the trocar in tissue and to control an amount of power output by the power source based on the determined insertion depth;
   wherein the antenna extends longitudinally within the shaft of the trocar.

10. The ablation system according to claim 9, wherein the distal end portion of the antenna is operably coupled to the second electrode of the trocar.

11. The ablation system according to claim 9, wherein the second electrode of the trocar is conical and configured to penetrate tissue.

12. The ablation system according to claim 9, wherein the first electrode is ring-like and at least partially encircles the shaft of the trocar.

13. The ablation system according to claim 9, wherein the antenna includes an inner conductor electrically connecting the power source and the second electrode.

14. The ablation system according to claim 13, further comprising a transmission line extending along an outer surface of the shaft of the trocar and electrically connecting the first electrode to the power source.

15. The ablation system according to claim 9, wherein the first electrode abuts the tubular outer surface of the proximal end portion of the shaft.

16. The ablation system according to claim 9, wherein the antenna has a distal end that terminates proximally of the second electrode.

17. An ablation device, comprising:
   an antenna including an inner conductor; and
   a trocar including:
   a shaft operably associated with a distal end portion of the antenna;
   a first electrode disposed on a proximal end portion of the shaft; and
   a second electrode forming a distal tip of the shaft and configured for insertion into tissue, the second electrode electrically connected to the inner conductor of the antenna, the proximal end portion of the shaft having a tubular outer surface formed with the distal tip, wherein the first and second electrodes are longitudinally spaced from one another along a longitudinal axis defined by the shaft.

* * * * *